United States Patent [19]

Kieturakis

[11] Patent Number: 5,752,973
[45] Date of Patent: May 19, 1998

[54] ENDOSCOPIC SURGICAL GRIPPING INSTRUMENT WITH UNIVERSAL JOINT JAW COUPLER

[75] Inventor: Maciej J. Kieturakis, San Carlos, Calif.

[73] Assignee: Archimedes Surgical, Inc., Menlo Park, Calif.

[21] Appl. No.: 324,998

[22] Filed: Oct. 18, 1994

[51] Int. Cl.[6] ................................................ A61B 17/28
[52] U.S. Cl. ...................... 606/207; 606/206; 606/205
[58] Field of Search ............................ 606/1, 138–147, 606/151, 167, 170, 205–211; 128/749–754

[56] References Cited

U.S. PATENT DOCUMENTS

| | | |
|---|---|---|
| 936,379 | 10/1909 | Stevens . |
| 3,096,962 | 7/1963 | Meijs . |
| 4,191,191 | 3/1980 | Auburn . |
| 4,535,773 | 8/1985 | Yoon .................................. 604/51 |
| 4,601,710 | 7/1986 | Moll .................................. 604/165 |
| 4,654,030 | 3/1987 | Moll et al. .......................... 604/165 |
| 4,836,205 | 6/1989 | Barrett . |
| 4,867,404 | 9/1989 | Harrington et al. . |
| 4,881,537 | 11/1989 | Henning ............................. 604/84 |
| 5,116,353 | 5/1992 | Green ................................. 606/184 |
| 5,147,316 | 9/1992 | Castillenti ........................... 604/164 |
| 5,147,376 | 9/1992 | Pianetti .............................. 606/170 |
| 5,201,325 | 4/1993 | McEwen et al. . |
| 5,203,773 | 4/1993 | Green ................................. 606/104 |
| 5,209,736 | 5/1993 | Stephens et al. .................... 604/164 |
| 5,209,747 | 5/1993 | Knoepfler ........................... 606/205 |
| 5,224,952 | 7/1993 | Deniega et al. ..................... 606/184 |
| 5,226,890 | 7/1993 | Ianniruberto et al. ................ 604/164 |
| 5,232,451 | 8/1993 | Freitas et al. ....................... 606/174 |
| 5,258,003 | 11/1993 | Ciaglia et al. ....................... 606/185 |
| 5,271,380 | 12/1993 | Riek et al. . |
| 5,279,567 | 1/1994 | Ciaglia et al. ....................... 604/117 |
| 5,284,130 | 2/1994 | Ratliff . |
| 5,312,357 | 5/1994 | Buijs et al. .......................... 604/164 |
| 5,334,185 | 8/1994 | Giesy et al. ......................... 604/164 |
| 5,336,237 | 8/1994 | Chin et al. .......................... 606/167 |
| 5,346,504 | 9/1994 | Ortiz et al. .......................... 606/192 |
| 5,348,541 | 9/1994 | Lyell .................................. 604/164 |
| 5,368,598 | 11/1994 | Hasson ............................... 606/119 |
| 5,370,109 | 12/1994 | Cuny . |
| 5,383,888 | 1/1995 | Zvenyatsky et al. ................. 606/205 |
| 5,405,344 | 4/1995 | Williamson et al. ................. 606/1 |
| 5,474,057 | 12/1995 | Makower et al. .................... 606/205 |
| 5,496,347 | 3/1996 | Hashiguchi et al. ................. 606/205 |

Primary Examiner—Glenn K. Dawson
Attorney, Agent, or Firm—Skjerven, Morrill, MacPherson, Franklin & Friel; Norman R. Klivans

[57] ABSTRACT

A surgical instrument for gripping tissue in an endoscopic workspace. The instrument has an elongate introducer sleeve extending along a primary axis. An articulating jaw assembly is coupled to the distal end of the introducer sleeve with a ball and socket-type joint that provides jaws that open and close with around a secondary axis. Thus, the secondary axis of the jaw assembly is free to articulate and rotate relative to the primary axis of the introducer sleeve. When tissue is gripped by the jaws, lateral retraction forces cause the jaw assembly to align itself with the direction of retracting forces. A trigger within a proximal handle actuates the jaws in any articulated position. The instrument further provides a "flex jaw" feature by which is meant the jaw working faces are somewhat free to rotate relative to the jaw arms. Thus, as the jaw arms close to grip tissue, the jaw working faces rotate to accommodate tissue thickness and density thereby uniformly apply gripping pressure on tissue.

27 Claims, 7 Drawing Sheets

FIG. 11

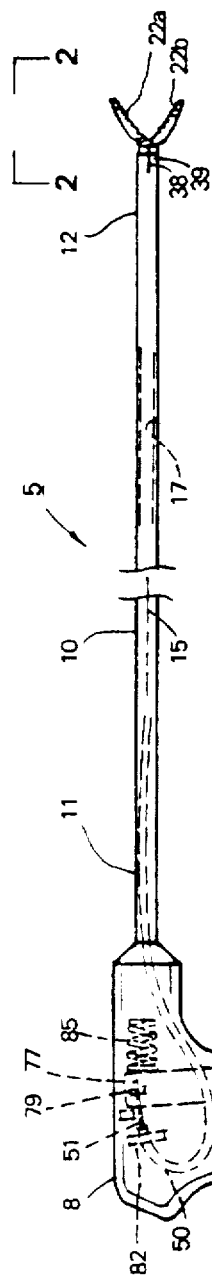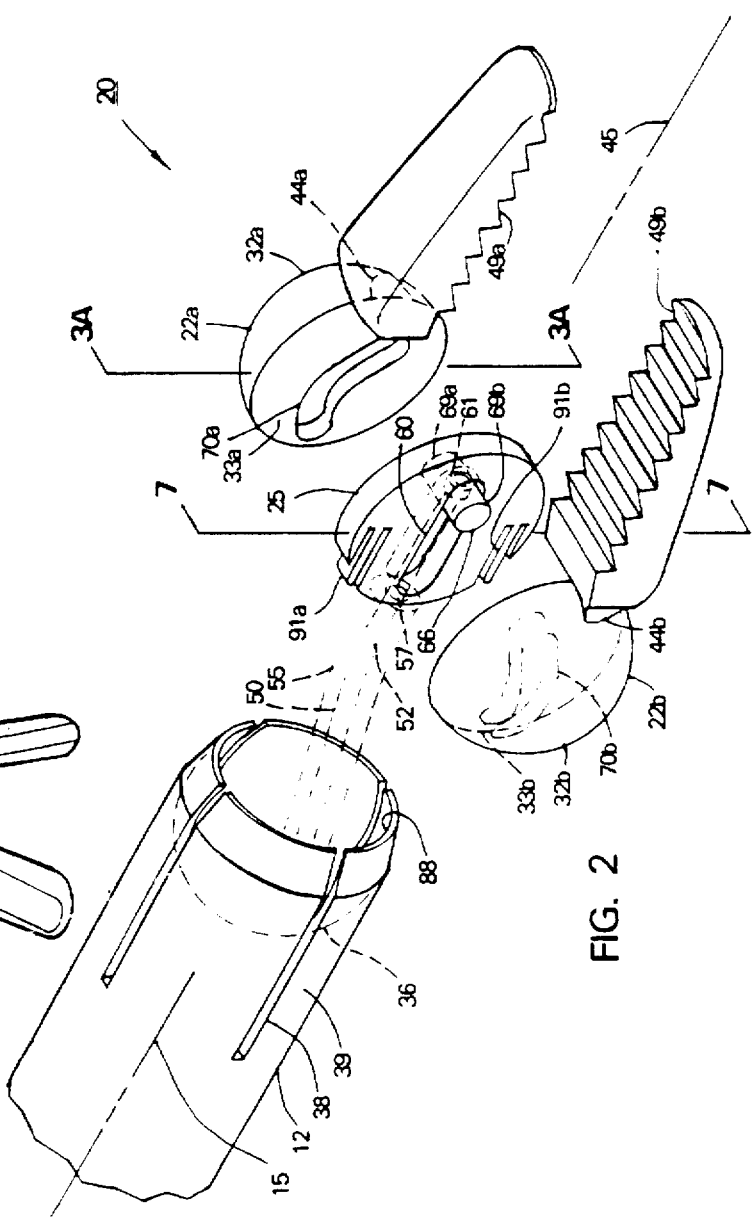
FIG. 1
FIG. 2

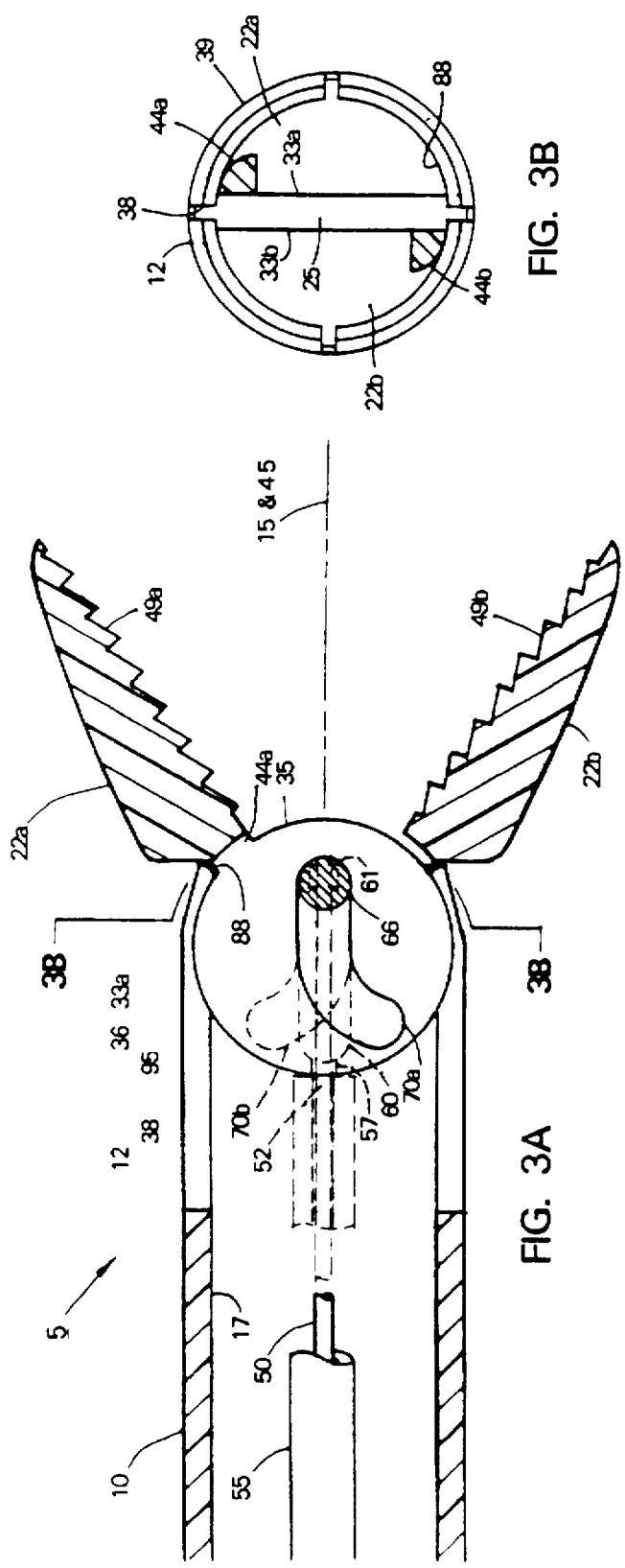

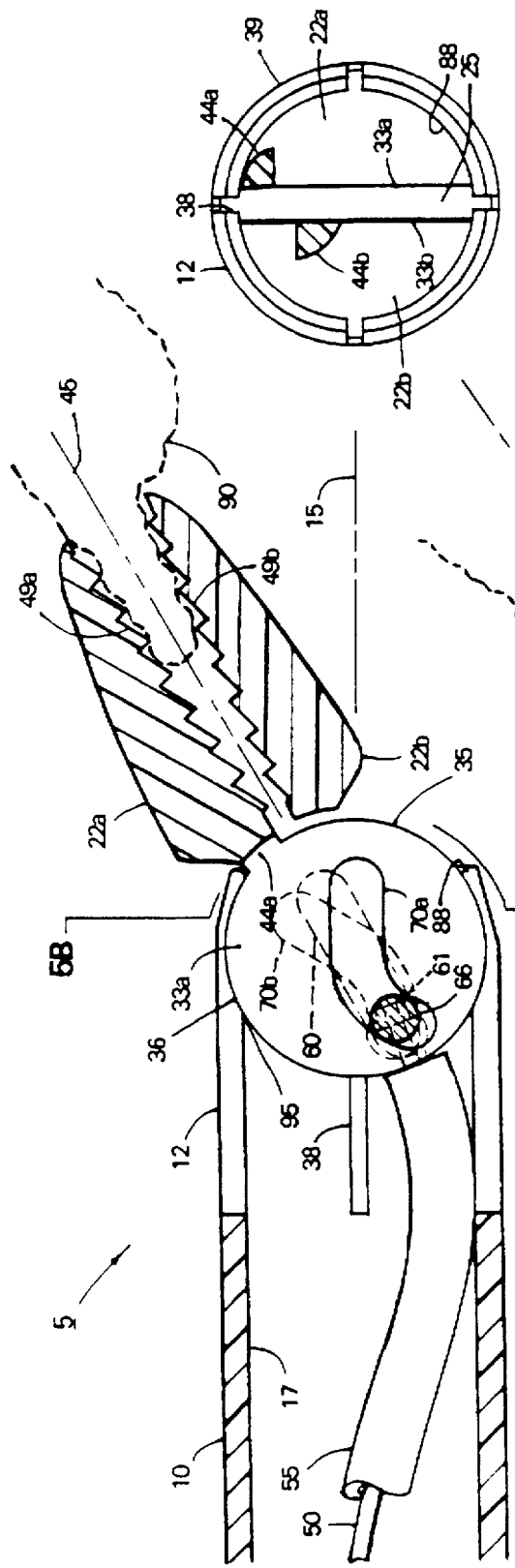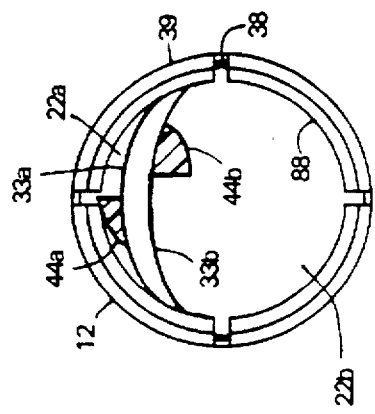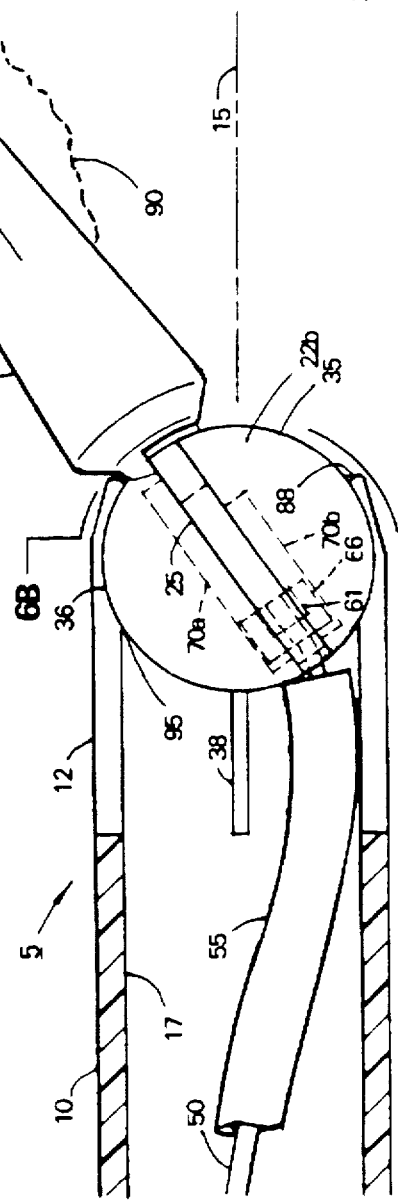

ENDOSCOPIC SURGICAL GRIPPING INSTRUMENT WITH UNIVERSAL JOINT JAW COUPLER

BACKGROUND OF THE INVENTION

1. Field of the Invention

This invention relates to surgical instrumentation and more particularly to an instrument for gripping and retracting tissue in an insufflated anatomic workspace.

2. Description of Prior Art

In a "minimally invasive" endoscopic surgery, for example in the abdominal cavity, all instrumentation is introduced through cannulas that are in stationary positions in the abdominal wall sometimes making it difficult to retract or reposition anatomic structures with elongate instruments (e.g., grippers). Two common problems are related to the rigid jaws found in commercially available gripping instruments. A first problem may be described with reference to an endoscopic cholecystectomy (gall bladder removal). It is necessary to retract the gall bladder laterally, that is, by swinging the instrument lateral to its axis rather moving the instrument axially. On occasion, such lateral movement will cause a distalmost tip of a jaw to perforate a wall of the gall bladder thus causing bile to spill into the abdominal cavity which is undesirable. Second, sometimes such rigid pivoting jaws will crush or perforate tissue in the proximalmost portion of the jaws while not yet firmly engaging tissue in the distalmost portion of the jaws which also is undesirable.

To avoid the above-described types of tissue damage, current practice often requires cannula placements that will insure that retraction forces are generally applied axially with respect to the cannula and the instrument disposed therein. Thus, it is sometimes necessary to make incisions for cannulas in difficult locations. It sometimes is necessary to make additional incisions for additional cannulas which also is undesirable. There is therefore a need for new instruments for gripping and retracting tissue in an endoscopic workspace.

SUMMARY OF THE INVENTION

The instrument of the present invention has an elongate introducer sleeve that is coupled to an articulating jaw assembly by a ball and socket-type joint that allows the jaw assembly to articulate and rotate about a second axis relative to the primary axis of the introducer sleeve. Thus, when tissue is engaged within the jaws, lateral retraction forces will cause the jaw assembly to articulate and the secondary axis of the jaw assembly will align itself with the direction of retracting forces. A trigger within a proximal handle actuates the jaws in any articulated position.

The instrument of the present invention further includes a "flex jaw" feature, by which is meant the jaw working faces are somewhat free to rotate relative to the jaw arms. Thus, as the jaw arms close to engage tissue, the jaw working faces rotate to accommodate tissue thickness and density thereby uniformly applying engaging pressures. The "flex-jaw" feature results from a plurality of pivoting points associated with the jaw assembly. The jaw arms open or close around a first proximal pivot while the jaw working faces rotate within limits around a second distal pivot.

In general, the instrument of the present invention provides an instrument for gripping and retracting tissue in which the jaw working faces close on an axis that will articulate to align itself with the direction of retraction forces. The present invention also provides an instrument in which the jaw assembly may rotate about the axis defined by the jaw assembly relative to the axis defined by the introducer member.

The present invention provides an instrument for retracting tissue in which the articulating jaw assembly is self-centering when the jaws are in an open position to align the secondary axis of the jaw assembly with the primary axis of the introducer member. The present invention also provides an instrument in which the articulating jaw assembly is self-centering when the jaws are in a closed position in the absence of retracting forces. The present invention also provides an instrument permitting the jaws to be locked in any articulated configuration after the jaws have engaged tissue. The present invention also provides an instrument that allows the secondary axis defined by the jaw assembly to be locked in parallel alignment with the primary axis of the elongate introducer member.

The present invention provides an instrument for gripping tissue that includes a "flex jaw" feature for applying engaging pressure on tissue uniformly over the jaw working ends regardless of the thickness of the engaged tissue. The present invention also provides an instrument in which the jaw working faces apply engaging pressure on tissue by utilizing a first pivot for rotating the jaw arms and a second pivot for rotating the jaw working faces.

Additional advantages and features of the invention appear in the following description in which several embodiments are set forth.

BRIEF DESCRIPTION OF THE DRAWINGS

FIG. 1 is an elevational view of the instrument of the present invention.

FIG. 2 is an exploded isometric view of an assembly of the instrument of FIG. 1 taken along line 2—2 of FIG. 1 rotated 90°.

FIG. 3A is a longitudinal partial sectional view of the assembly of FIG. 2 taken along line 3A—3A of FIG. 2 in a certain position.

FIG. 3B is a transverse sectional view of the assembly of FIG. 3A taken along line 3B—3B of FIG. 3A.

FIG. 4A is a longitudinal partial sectional view of the assembly of FIG. 2 taken along line 3A—3A of FIG. 2 in an alternative position.

FIG. 4B is a transverse sectional view of the assembly of FIG. 4A taken along line 4B—4B of FIG. 4A.

FIG. 5A is a longitudinal partial sectional view of the assembly of FIG. 2 taken along line 3A—3A of FIG. 2 in an alternative position.

FIG. 5B is a transverse sectional view of the assembly of FIG. 5A taken along line 5B—5B of FIG. 5A.

FIG. 6A is a longitudinal partial sectional view of the assembly of FIG. 2 taken along line 3A—3A of FIG. 2 in an alternative position.

FIG. 6B is a transverse sectional view of the assembly of FIG. 6A taken along line 6B—6B of FIG. 6A rotated 90°.

DESCRIPTION OF PREFERRED EMBODIMENTS OF THE INVENTION

Figure 8:
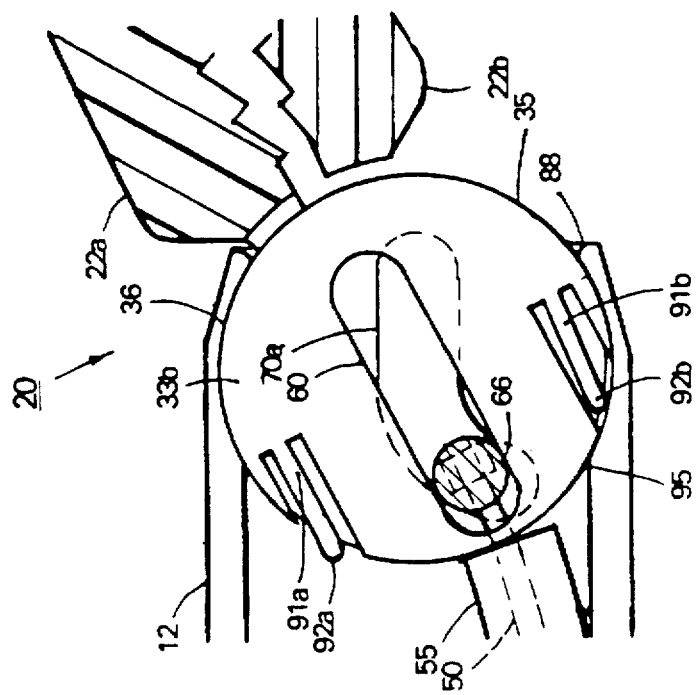
FIGS. 7–8 are longitudinal sectional views illustrating a component part of the subassembly of FIG. 2 taken along line 7—7 of FIG. 2 in alternative positions.

By way of example, FIG. 1 depicts instrument 5 with handle assembly 8 coupled to elongate introducer sleeve 10. Sleeve 10 with proximal and distal ends respectively 11 and 12, has a cylindrical shape extending along axis 15 with an overall length of approximately 200 mm. (not limiting). The outside diameter of sleeve 10 is approximately 10 mm. (not limiting) to cooperate with a standard 10–11 mm. inside diameter cannula. Sleeve 10 is made of any suitable material such as injection-molded plastic or a combination of metal and plastic. Bore 17 extends through sleeve 10.

Referring to FIGS. 1–2, jaw assembly 20 is carried at distal end 12 of sleeve 10 and includes cooperating left-hand and right hand jaw elements, 22a and 22b, respectively. The jaw elements, 22a and 22b, are made of any suitable material such as e.g. injection-molded plastic or metal. Actuator disc 25 fits between jaw elements, 22a and 22b, and disc 25 is made of e.g. an injection-molded plastic that has resilient characteristics, such as Delrin. The proximal hemispherical portions 32a and 32b of jaw elements 22a and 22b have opposing flat faces 33a and 33b respectively. The assembly of proximal hemispherical portions 32a and 32b of the jaw elements together with actuator disc 25 form a spheroid-shaped portion 35 of assembly 20 (see FIGS. 3A–3B).

Spheroid-shaped portion 35 of assembly 20 slip fits in cooperating spheroid-shaped socket 36 formed within distal end of bore 17 of sleeve 10 (see FIGS. 2 and 3A–3B). A plurality of longitudinal slots 38 allow for flexing of longitudinally-extending socket portions 39 in sleeve 10. Such socket portions 39 may flex slightly radially outward to insert spheroid-shaped portion 35 into spheroid-shaped socket 36. Thus, jaw assembly 20, and more particularly spheroid-shaped portion 35, may articulate and rotate in socket 36.

Referring to FIG. 2, jaw elements 22a and 22b have distal jaw arms 42a and 42b. Arms 42a and 42b are connected to proximal hemispherical portions 32a and 32b, respectively, by web portions 44a and 44b. The jaw elements, and more particularly the jaw arms 42a and 42b, converge on or separate from secondary axis 45 of jaw assembly 20. The arms of each jaw element are configured to extend laterally across secondary axis 45 such that working faces 49a and 49b mate symmetrically relative to secondary axis 45 (see FIGS. 2 and 6A).

A mechanism is provided to actuate jaw assembly 20 between an open position (see FIG. 3A) and a closed position (see FIG. 4A). The jaw actuating mechanism includes flexible cable 50 with proximal and distal ends respectively 51 and 52, that extends through flexible cable housing 55. Cable 50 is made of any suitable material such as braided stainless steel and extends through aperture 57 in actuator disc 25 and thereafter into longitudinal slot 60 in disc 25. The distal end 52 of cable 50 is press fit with crimp nut 61 and the crimp nut 61 is press fit into cylindrical cross-bar 66. Cross-bar 66 is dimensioned to slide to and fro in elongate slot 60 in actuator guide disc 25. Cross-bar 66 has left and right ends 69a and 69b respectively, that extend beyond the respective flat sides of guide disc 25. When jaw assembly 20 is assembled, the left end 69a of cross-bar 66 engages arcuate slot 70a in flat face 33a of left-hand jaw 22a. Similarly, the right end 69b of cross-bar 66 engages arcuate slot 70b in flat face 33b of right-hand jaw 22b.

Trigger 75 is provided within handle 8 to apply axial forces on cable 50 to actuate the jaw elements between open and closed positions. Referring to FIG. 1, the proximal end 51 of cable 50 along with cable housing 55 extends through bore 17 into the hollow core of plastic handle 8 that is made of mating halves. Trigger 75 rotates around pivot pin 76 to pull cable 50 in the proximal direction. More particularly, the proximal end 51 of cable 50 is fixed in upper arm portion 77 of trigger 75 with crimp nut 79. Cable housing 55 is fixed in molded cable stop 82 within handle 8. Thus, squeezing trigger 75 causes cable 50 to move proximally relative to cable housing 55. Compression spring 85, shown in phantom view in FIG. 1, urges trigger 75 toward the non-depressed (jaw-open) position.

Referring now to FIGS. 3A–3B and 4A–5B, it can be seen that the proximal and distal movement of cable 50 relative to cable housing 55 causes left-hand and right-hand jaw elements 22a and 22b to open and close. FIGS. 3A–3B and 4A–4B are sectional views taken along flat face 33a of left hand jaw element 22a looking away depicting left-hand arcuate slot 70a in plan view. In the aforementioned figures, cooperating elongate slot 60 and arcuate slot 70b of right-hand jaw element 22b are shown in phantom view for explanatory purposes.

In FIG. 3A, spring 85 has urged cable 50 and cross-bar 66 distally relative to the distal end of cable housing 55 that abuts the proximal part of guide disc 25. FIG. 3A shows cross-bar 66 in a distal position in longitudinal slot 60 with left and right ends 69a and 69b of cross-bar 66 having a camming effect as the cross-bar contacts the edges of arcuate slots 70a and 70b. Thus, the camming effect of cross-bar 66 within arcuate slots 70a and 70b causes left-hand and right-hand jaw elements 22a and 22b, and more particularly the hemispherical proximal portions 32a and 32b, to counter-rotate in socket 36. Such counter-rotation causes jaw arms 42a and 42b to open away from secondary axis 45.

Referring now to FIG. 4A, it can be seen that cable 50 is pulled proximally by trigger 75 and cross-bar 66 has a camming effect as the cross-bar moves proximally in arcuate slots 70a and 70b, thus causing the hemispherical proximal portions 32a and 32b to counter-rotate in socket 36 and thereby further causing jaw arms 42a and 42b to close toward secondary axis 45. The contours and radii of arcuate slots 70a and 70b typically are identical except for being reversed relative to axis 45. It should be noted, however, that the contours and radii of such arcuate slots may vary to provide jaws that move asymmetrically in a variety of manners with respect to secondary axis 45 for special gripping applications.

Of particular interest to the present invention, jaw assembly 20 includes an "open-jaw self-centering" mechanism. By the term self-centering, it is meant that a mechanism is provided to align secondary (jaw) axis 45 with primary axis 15 of introducer sleeve 10 when the jaws are actuated to the open position (see FIG. 3A). This feature is desirable since the jaw elements are in the closed position (see FIG. 4A) for introduction through a cannula. As the jaws are then opened in an endoscopic workspace inside the body, the secondary (jaw) axis 45 preferably is aligned with primary axis 15 for approaching tissue to be gripped. As can be seen in FIG. 3B, the self-centering of the open jaws occurs as jaw elements 22a and 22b are urged by spring 85 to counter-rotate, which counter-rotation is limited as webs 44a and 44b abut the circular periphery of distal aperture 88 of spherical-shaped socket 36. Webs 44a and 44b are symmetrical relative to the corresponding arcuate slots 70a and 70b thus causing secondary axis 45 to align with primary axis 15 when the jaws are in the open position.

Referring now to FIGS. 5A–5B and 6A–6B, it is now possible to describe jaw assembly 20 as it articulates to align itself and secondary axis 45 with the direction of retraction forces. FIG. 5A depicts tissue 90 engaged between working faces 49a and 49b of jaw elements 22a and 22b, respectively, as tissue 90 is being retracted. Since spheroidal-shaped portion 35 of jaw assembly 20 enjoys a slip-type fit in spheroid-shaped socket 36, axis 45 naturally will align itself with the direction of retraction forces. Note that cable 50 and cable housing 55 have sufficient slack in overall length with bore 17 to not interfere with the articulation of jaw assembly 20. FIG. 5B shows the limit of articulation as web 44a abuts the circular periphery of aperture 88.

Of particular interest to the present invention, jaw assembly 20 may rotate in 360° relative to sleeve 10. FIGS. 6A shows jaw assembly 20 articulating at a different angle from that shown in FIG. 5A. FIG. 6B shows the limit of articulation as web 44a abuts the circular periphery of aperture 88 at a different angle. Thus, after gripping tissue 90 within jaw assembly 20, the tissue may be retracted in any direction, or the direction of retraction may be varied, and jaw assembly 20 will articulate and/or rotate allowing axis 45 to remain continuously aligned with the direction of retraction forces.

Figure 7:
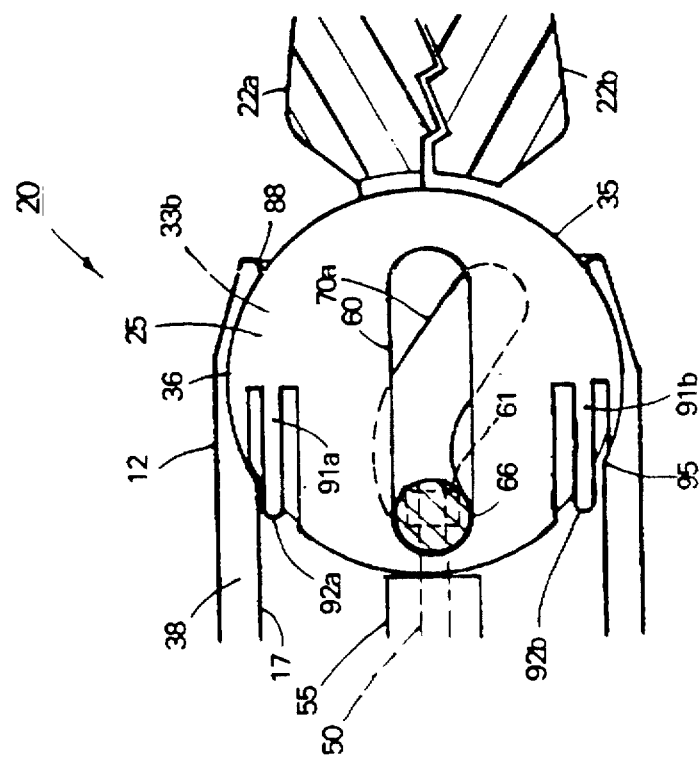

Also of particular interest to the present invention, jaw assembly 20 includes a "closed-jaw self-centering" mechanism to maintain secondary axis 45 in alignment with primary axis 15 when the jaw elements are in the closed position as shown in FIG. 6A. This feature is desirable, for example, when jaw elements 22a and 22b are actuated to the closed position for introduction through a cannula, in which case it is desirable to have jaw assembly 20 stabilized rather than free to articulate. The closed-jaw centering mechanism maintains jaw assembly 20 in the "centered" position of FIG. 6A, but such "centered" position can be overcome by a slight force. Referring to FIGS. 7–8, actuator disc 25 is injection-molded of resilient plastic material and formed with spring arms 91a and 91b. The spring arms have tips, 92a and 92b, that extend slightly outward beyond the circular periphery of disc 25. Thus, the tips 92a and 92b abut the wall of sleeve 10 that defines bore 17 adjacent to proximal edge 95 of socket 36 as shown in FIG. 7 to maintain the secondary (jaw) axis 45 in alignment with primary axis 15. As jaw elements 22a and 22b are moved to the open position from the closed position, actuator disc 25 will remain in the "centered" position. When retracting force causes jaw assembly 20 to articulate at any angle in 360° around axis 15, such force will cause either or both tips 92a and 92b of the spring arms to abut the wall of bore 17 adjacent to proximal edge 95 of socket 36 before such force overcomes the spring constant of arms 91a and/or 91b, thus permitting the spring arm(s) to bend and fit within socket 36. FIG. 8 depicts tip 92b of spring arm 91b bending to fit in socket 36 as jaw assembly 20 articulates. Such overcoming forces are preferably slight and depend only on the spring constant formed into spring arms 91a and 91b.

Figure 9:
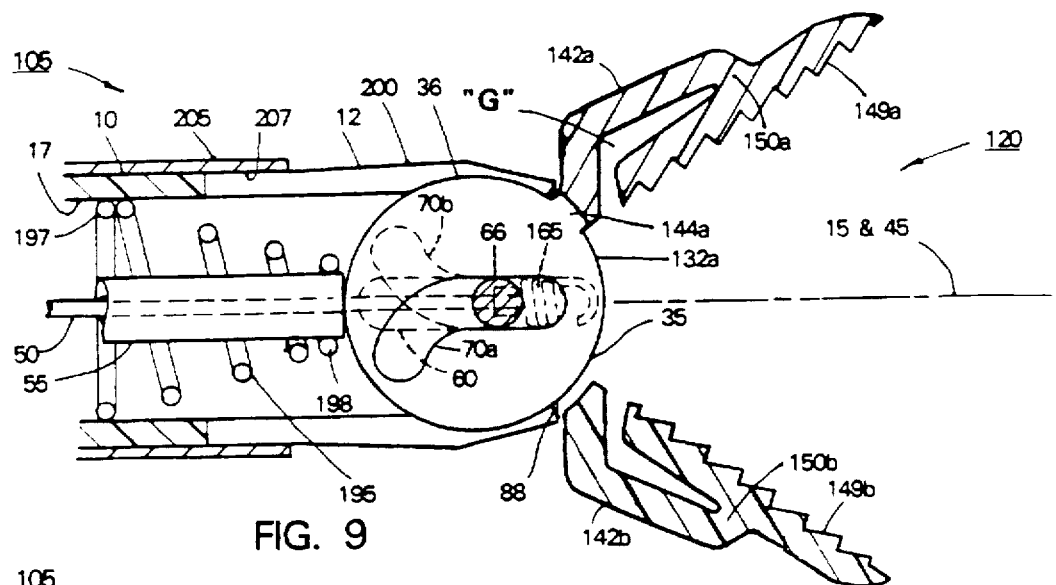
FIG. 9 is a longitudinal partial sectional view of a second embodiment of gripping assembly similar to the views of FIGS. 4A–6A.

FIG. 9 depicts a second embodiment of gripper 105 with an articulating jaw assembly in which like reference numerals refer to elements common to the previously described first embodiment of FIGS. 1–6B. Gripper 105 differs from the first-described embodiment principally in that it incorporates jaw elements that have a "flex-jaw" feature, by which is meant the jaw elements uniformly apply engaging pressure on tissue along the length of the jaw working faces.

Figure 10:
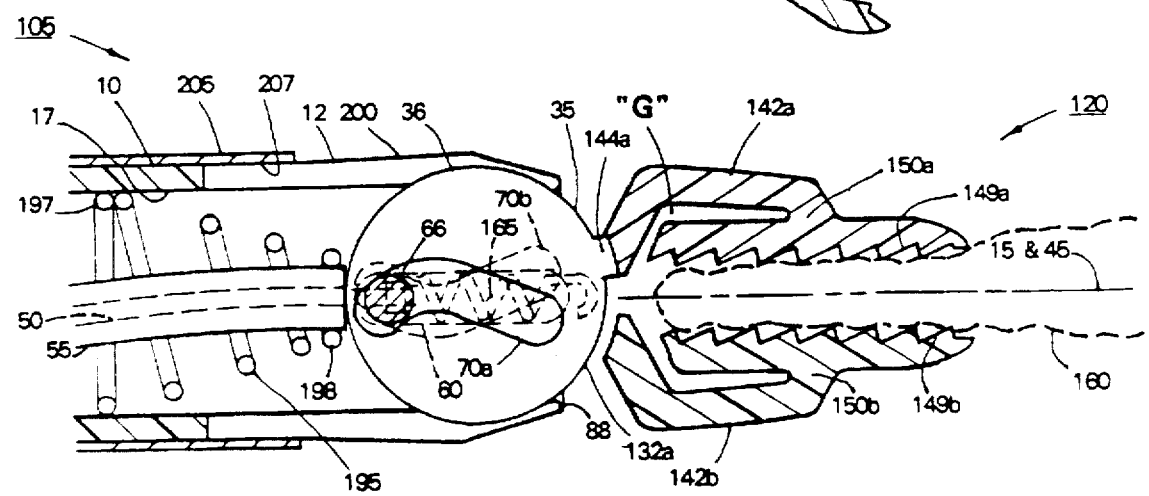
FIG. 10 is a longitudinal partial sectional view of the assembly of FIG. 9 in another position.
Figure 11:
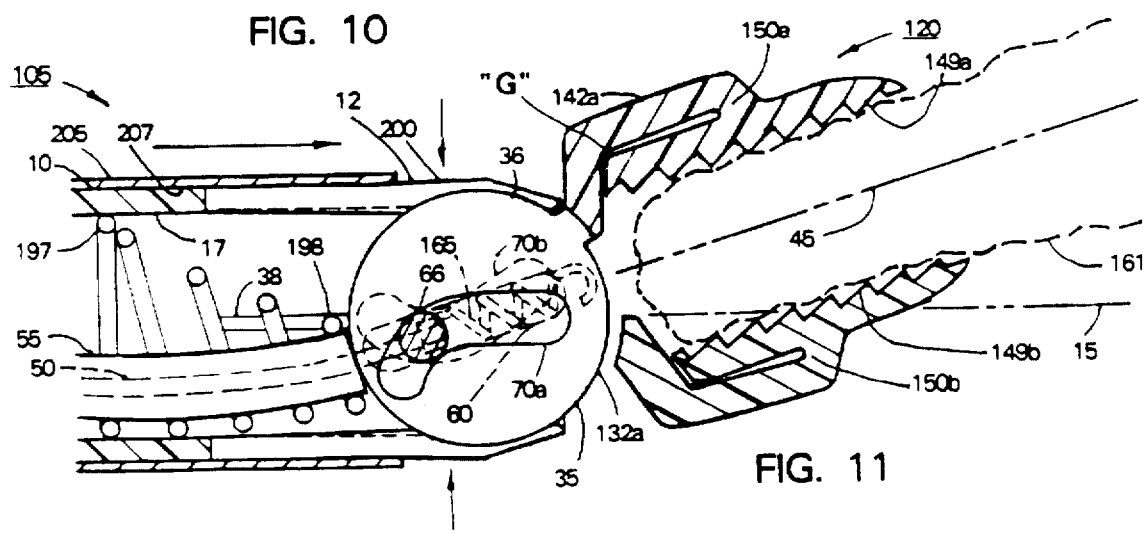
FIG. 11 is a longitudinal partial sectional view of the assembly of FIG. 9 in yet another position.

Referring to FIGS. 9–11, the alternative jaw assembly 120 is similar to the first-described embodiment including left-hand and right-hand jaw elements 122a and 122b, proximal hemispherical portions 132a and 132b, and jaw arms 142a and 142b that are e.g. unitary molded plastic (e.g., Delrin). The jaw arms are connected to proximal hemispherical portions 132a and 132b by rigid webs 144a and 144b respectively. In this embodiment, working faces 149a and 149b are connected to jaw arms 142a and 142b by unitary flexible hinge portions 150a and 150b. The flexibility of hinge portions 150a and 150b is dependent on the cross-sectional dimension and composition of the resilient plastic or other material. FIG. 9 is a sectional view of working faces 149a and 149b in a repose position with gap "G" indicating a limit on flexing the working faces. FIG. 10 depicts jaw working faces 149a and 149b gripping tissue 160 that is thin in cross-section with the working faces pivoting slightly around hinge portions 150a and 150b thus applying engaging pressure over the length of the working faces. As can be seen in FIG. 10, gap "G" is reduced in dimension to accommodate rotation of the working faces. FIG. 11 depicts working faces 149a and 149b gripping tissue 161 that is thick in cross-section with working faces rotated around hinge portions 150a and 150b with gap "G" shown in a corresponding reduced dimension.

Figure 12:
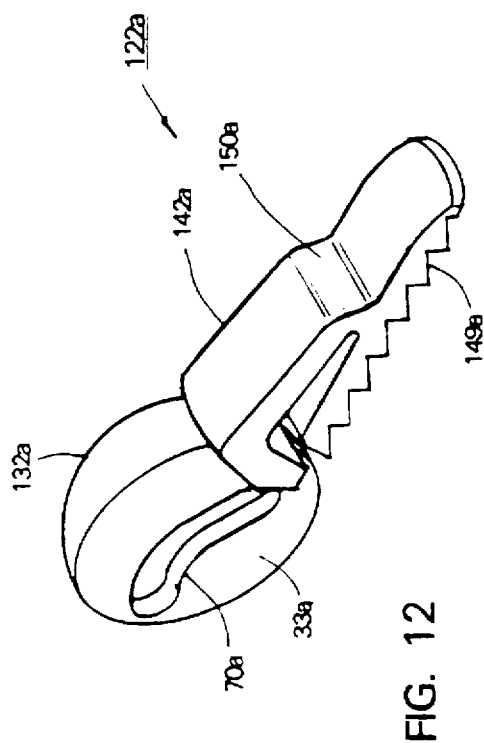
FIG. 12 is an isometric view of a component part of the second embodiment of FIG. 9.

Of particular interest to the present invention, left-hand and right-hand jaw elements 122a and 122b may be injection-molded sequentially from a single mold. Referring to FIG. 12, left-hand jaw element 122a with arcuate slot 70a is shown in isometric view. It can be seen that the left-hand jaw element 122a can be flipped over thus providing a right-hand jaw element 122b (not shown) with slot 70a then re-designated as slot 70b. It should be noted that using a single mold for both left-hand and right-hand jaw elements is best utilized with somewhat smooth jaw working faces, because "alligator-tooth" working faces then will not mesh.

Figure 13:
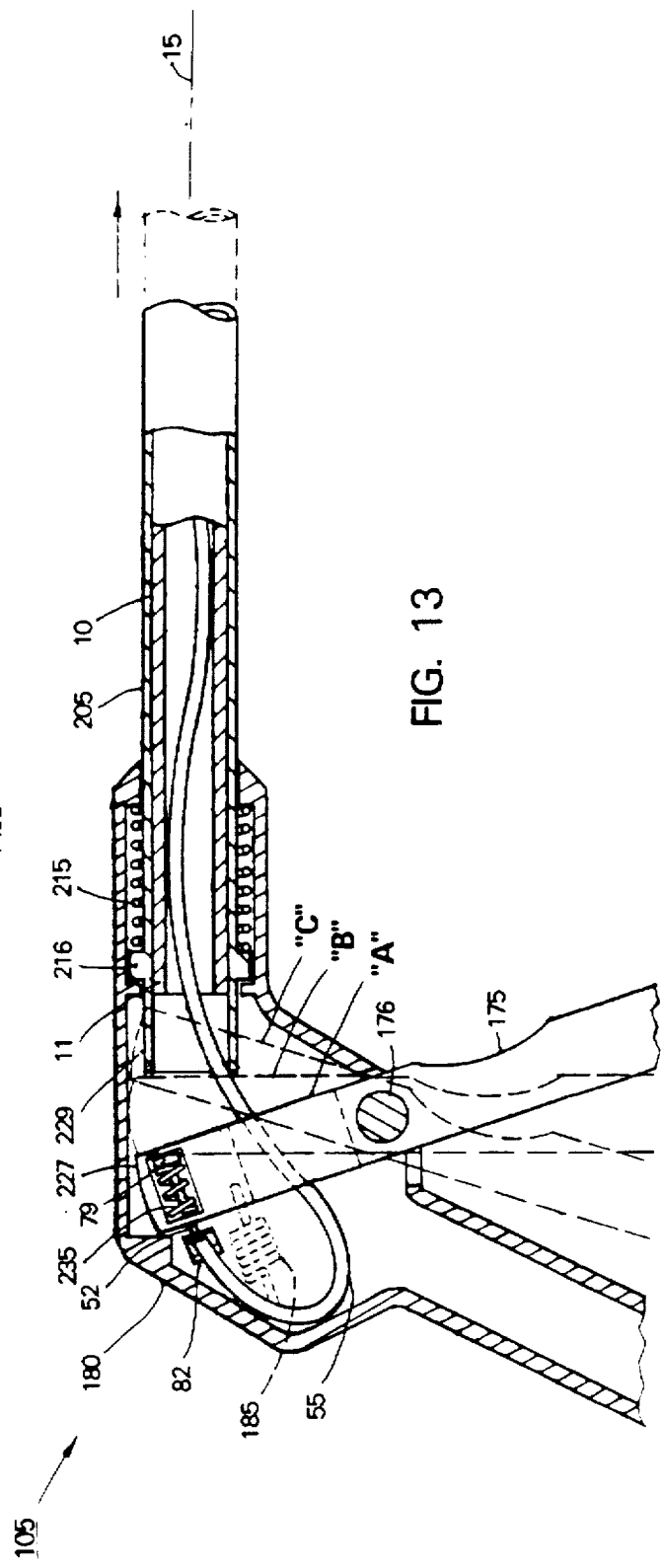
FIG. 13 is a partial sectional view of the handle of the second embodiment referred to in FIGS. 9–12.

Referring to FIGS. 9 and 13, the second embodiment of gripper 105 offers alternative locations for springs to urge left-hand and right-hand jaw elements 122a and 122b toward the open position. FIG. 9 shows in phantom view an extension spring 165 disposed in longitudinal slot 60. Spring 165 is connected to and pulls cross-bar 66 in the distal direction thus actuating the jaw elements to the open position by means of the camming effect on arcuate slots 70a and 70b as described above. Referring to FIG. 12, trigger 175 pivoting around pivot pin 176 is provided within handle 180 and may additionally apply springing axial forces on cable 50 as described in the first embodiment. Trigger 175 may be urged toward the non-depressed "A" position in plan view in FIG. 13 by extension spring 185 (in phantom view) thus additionally actuating the jaw elements toward the open position.

Referring to FIGS. 10–11, the second embodiment of gripper 105 provides an alternative "self-centering" mechanism to maintain secondary axis 45 in alignment with primary axis 15 in both the open-jaw and closed-jaw positions. The self-centering mechanism comprises conical-shaped helically wound spring 195. The proximal end of spring 197 generally is press fit in bore 17 of sleeve 10 while distal end 198 generally is press fit around the distal end of cable housing 55. As shown in FIG. 11, articulation of jaw assembly 120 tensions spring 195 by lateral movement of distal end 198 and spring 195 will urge the jaw assembly back toward the "centered" position as shown in FIG. 10.

Referring still to FIGS. 9-11, gripper 105 offers a locking mechanism to lock jaw assembly 120 in an articulated position or a non-articulated position. Such a locking mechanism may be utilized, for example, to lock and rotate tissue while being retracted laterally to better dissect around the tissue. The distal end 12 of sleeve 10 is configured with a distal inclined portion 200 that exhibits a slight increase in cylindrical dimension toward the distal direction. In distal inclined portion 200, the longitudinal slots 38 define longitudinal-extending socket portions 39. A reciprocating sleeve 205 with bore 207 is made of thin-wall metal or plastic and is slidably disposed around introducer sleeve 10.

Referring to FIG. 11, it can be seen that the distal sliding of reciprocating sleeve 205 will press the socket portions radially inward to frictionally grip spheroid-shaped portion 35 of jaw assembly 120. Reciprocating sleeve 205 is actuated proximally or distally by means within handle 180 (see FIG. 13). FIG. 13 shows the proximal end of reciprocating sleeve 205 mounted around introducer sleeve 10. Sleeve 10 is fixed in relationship to handle 180 by elements extending through slots in reciprocating sleeve 205 (not visible). Reciprocating sleeve 205 is urged toward the proximal position by compression spring 215 abutting unitary flange 216 formed into sleeve 205. Trigger 175 actuates reciprocating sleeve 205 distally to lock jaw assembly 120 in any articulated position (see FIG. 11) when upper trigger arm 227 abuts and pushes distally the proximal end 229 of sleeve 205. FIG. 13 shows trigger 175 in plan view in a non-depressed "A" position, with phantom views of trigger 175 in an intermediate "B" position and a fully depressed "C" position. Trigger 175 actuates the jaw elements from the open to closed position as it moves from the "A" position to the "B" position. When trigger 175 is actuated from the "B" position toward the "C" position, such actuation forces will overcome the strength of compression spring 235 that is disposed around cable 50 and abuts crimp nut 79 within upper trigger arm 227. Thus, it can be seen that after trigger 175 is moved beyond the "B" position toward the "C" position, upper trigger 227 arm will contact proximal end 229 of reciprocating sleeve 205 and push the sleeve distally to lock jaw assembly 120 in any articulated position.

Referring to FIG. 12, it should be appreciated that a jaw element with a "flex-jaw" feature similar to jaw element 220a may be made with a pin-type hinge (not shown) as a pivot point between jaw arm 244a and working face 249a and be within the scope of the present invention. Referring still to FIG. 12, the previously-described actuation mechanism for jaw structures that includes a camming cross-bar 66 and arcuate slots 70a and 70b may be utilized in grippers that do not include an articulating jaw assembly. For example, a gripper may have left-hand and right-hand jaw elements similar to element 122a of FIG. 12 except that the proximal portions of the left-hand and right-hand jaw elements form a cylindrical shape that rotates in cooperating cylindrical-shaped socket.

Figure 14:
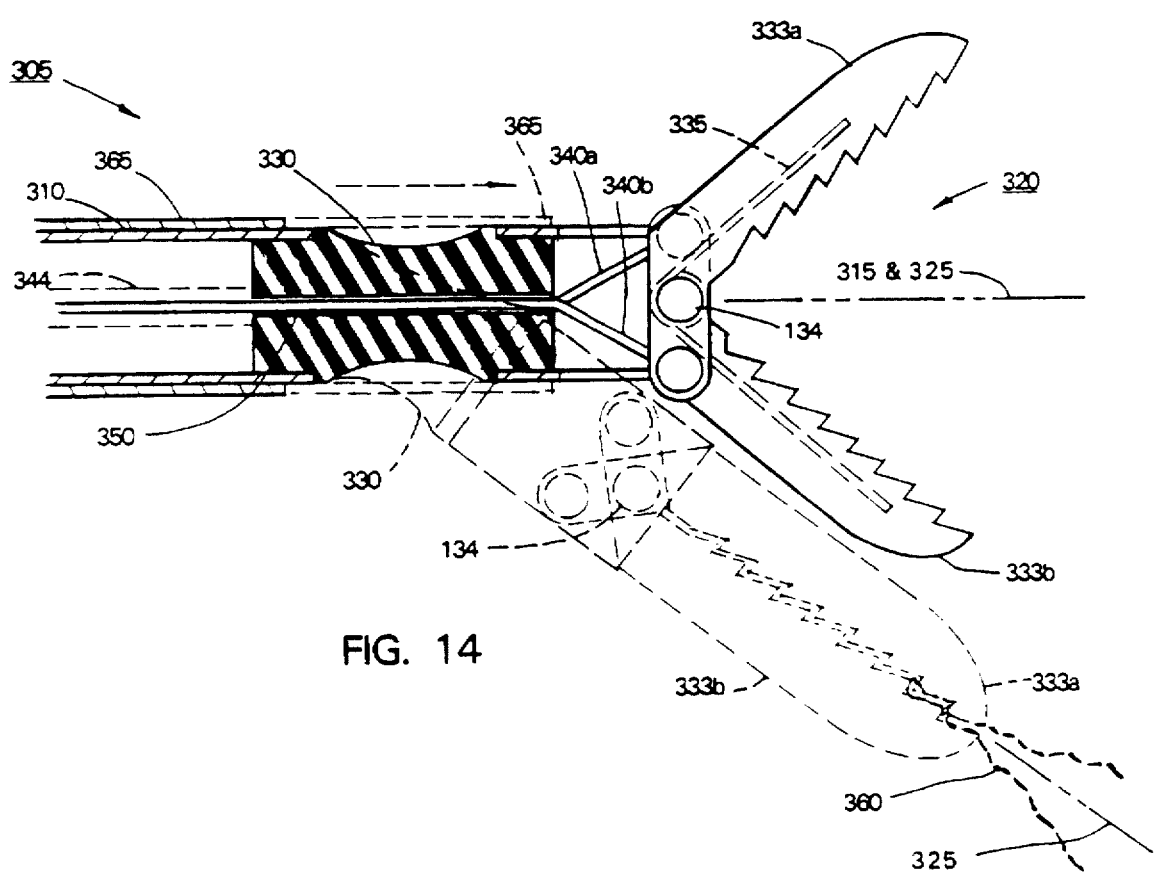
FIG. 14 is a partial sectional view of a portion of a third embodiment of gripping instrument.

FIG. 14 illustrates a third embodiment of gripper 305 that incorporates an introducer sleeve 310 extending along primary axis 315 coupled to jaw assembly 320 that closes on secondary axis 325. The secondary axis 325 may articulate relative to primary axis 315. In this embodiment, the flexible connection between sleeve 310 and jaw assembly 320 is a flexible universal joint 330 made of any suitable resilient material such as urethane. In FIG. 14, it can be seen that jaw elements 333a and 333b rotate around pin 334. The jaw elements are urged to the open position by torsion spring 335 shown in phantom view. Flexible braided steel cables 340a and 340b are disposed in cable housing 344 for actuating the jaws to the closed position. The distal end of cable housing 344 abuts the proximal end of universal joint 330 and cable 340a and 340b extend through bore 350 in the universal joint. Thus, it can be seen that proximal movement of cables 340a and 340b relative to cable housing 344 will actuate jaw elements 333a and 333b to the closed position.

Still referring to FIG. 14, it can be seen in phantom view that universal joint 330 may flex. When gripper 305 is utilized to retract tissue 360 laterally relative to primary axis 315, the universal joint will articulate allowing secondary axis 325 of jaw assembly 320 to align itself with the direction of retraction forces. It should be appreciated that gripper 305 may be fitted with a metal universal-type joint (not shown) of the type that has multiple pivots and be within the scope of the present invention. It should be further appreciated that gripper 305 may be fitted with a universal-type joint (not shown) of the type that has a helically-wound spring connecting proximal and distal portions of an introducer sleeve thus providing flexibility and be within the scope of the present invention.

Of particular interest to the present invention, referring to FIG. 14, thin-wall reciprocating sleeve 365 may be slidably mounted around introducer sleeve 310. When reciprocating sleeve 365 is slid distally to extend over universal joint 330 and maintained in such a position as shown in phantom view, the flexibility of universal joint 330 will be disabled. Thus, a single gripper 305 is provided that selectively offers either a rigid-axis jaw assembly or an articulating-axis jaw assembly. Further, it should be appreciated that reciprocating sleeve 365 may have a distal rest position thereby disabling universal joint 330 and the sleeve 365 may be actuatable in the proximal direction by the trigger mechanism (not shown) that actuates jaw elements 333a and 333b toward the closed position. Thus, universal joint 330 may be disabled while said jaws move from the open position toward the closed position until a certain degree of closure is reached, after which universal joint 330 is free to articulate as sleeve 365 moves proximally.

This disclosure is illustrative and not limiting. Further variations will be apparent to one skilled in the art in light of this disclosure and are intended to fall within the scope of the appended claims.

I claim:

1. A surgical instrument comprising:

a handle;

an elongate introducer member defining a first axis and having proximal and distal ends, a proximal end of said introducer member extending from said handle;

a universal joint at said distal end of said introducer member;

two opposing jaws each depending from said universal joint, said jaws defining a second axis and being movable between a closed position wherein said jaws converge toward said second axis and an open position wherein said jaws separate away from said second axis, whereby said universal joint allows said second axis to move relative to said first axis between parallel and non-parallel relationships in response to forces on said introducer member and said jaws; and a jaw-actuating structure operatively connected to said jaws for causing said jaws to move between the open and closed positions with said jaws and said introducer member in a parallel or a non-parallel relationship;

wherein said universal joint includes a helically wound spring.

2. A surgical instrument comprising:

a handle;

an elongate introducer member defining a first axis and having proximal and distal ends, a proximal end of said introducer member extending from said handle;

a universal joint at said distal end of said introducer member;

two opposing jaws each depending from said universal joint, said jaws defining a second axis and being movable between a closed position wherein said jaws converge toward said second axis and an open position wherein said jaws separate away from said second axis, whereby said universal joint allows said second axis to move relative to said first axis between parallel and non-parallel relationships in response to forces on said introducer member and said jaws; and a jaw-actuating structure operatively connected to said jaws for causing said jaws to move between the open and closed positions with said jaws and said introducer member in a parallel or a non-parallel relationship;

a self-aligning mechanism operatively connected to said jaws, thereby maintaining said second axis as defined by said jaws in substantial alignment with said first axis when said jaws are in the open position; wherein said universal joint comprises a ball and a socket, and said self-aligning mechanism comprises portions of said jaws symmetrically abutting an edge of an aperture in the socket of said ball and socket joint.

3. The instrument of claim 2, wherein said self-aligning mechanism comprises at least one spring disposed within said introducer member that urges said second axis, as defined by said jaws, into alignment with said first axis.

4. A surgical instrument comprising:

a handle;

an elongate introducer member defining a first axis and having proximal and distal ends, a proximal end of said introducer member extending from said handle;

a universal joint at said distal end of said introducer member;

two opposing jaws each depending from said universal joint, said jaws defining a second axis and being movable between a closed position wherein said jaws converge toward said second axis and an open position wherein said jaws separate away from said second axis, whereby said universal joint allows said second axis to move relative to said first axis between parallel and non-parallel relationships in response to forces on said introducer member and said jaws;

a jaw-actuating structure operatively connected to said jaws for causing said jaws to move between the open and closed positions with said jaws and said introducer member in a parallel or a non-parallel relationship; and a jaw self-aligning mechanism operatively connected to said jaws, thereby releasably maintaining said second axis defined by said jaws in substantial alignment with said first axis when said jaws are moved toward the closed position from the open position;

wherein said universal joint comprises a ball and a socket and said self-aligning mechanism comprises a plurality of spring elements incorporated into proximal portions of said jaws that releasably engage an edge portion of said socket.

5. A surgical instrument comprising:

a handle;

an elongate introducer member defining a first axis and having proximal and distal ends, a proximal end of said introducer member extending from said handle;

a universal joint at said distal end of said introducer member;

two opposing jaws each depending from said universal joint, said jaws defining a second axis and being movable between a closed position wherein said jaws converge toward said second axis and an open position wherein said jaws separate away from said second axis, whereby said universal joint allows said second axis to move relative to said first axis between parallel and non-parallel relationships in response to forces on said introducer member and said jaws;

a jaw-actuating structure operatively connected to said jaws for causing said jaws to move between the open and closed positions with said jaws and said introducer member in a parallel or a non-parallel relationship; and a locking mechanism operatively connected to said jaws for releasably locking said jaws in a position such that said second axis is in alignment with said first axis.

6. A surgical instrument comprising:

a handle;

an elongate introducer member defining a first axis and having proximal and distal ends, a proximal end of said introducer member extending from said handle;

a universal joint at said distal end of said introducer member;

two opposing jaws each depending from said universal joint, said jaws defining a second axis and being movable between a closed position wherein said jaws converge toward said second axis and an open position wherein said jaws separate away from said second axis, whereby said universal joint allows said second axis to move relative to said first axis between parallel and non-parallel relationships in response to forces on said introducer member and said jaws;

a jaw-actuating structure operatively connected to said jaws for causing said jaws to move between the open and closed positions with said jaws and said introducer member in a parallel or a non-parallel relationship; and a reciprocating sleeve slidably mounted around said introducer member, wherein a slidable disposition of said reciprocating sleeve over said universal joint locks said universal joint.

7. A surgical instrument comprising:

a handle;

an elongate introducer member defining a first axis and having proximal and distal ends, a proximal end of said introducer member extending from said handle;

a universal joint at said distal end of said introducer member;

two opposing jaws each depending from said universal joint, said jaws defining a second axis and being movable between a closed position wherein said jaws converge toward said second axis and an open position wherein said jaws separate away from said second axis, whereby said universal joint allows said second axis to move relative to said first axis between parallel and non-parallel relationships in response to forces on said introducer member and said jaws; and a jaw-actuating structure operatively connected to said jaws for causing said jaws to move between the open and closed positions with said jaws and said introducer member in a parallel or a non-parallel relationship;

each said jaw further including a hinge located intermediate its distal end and said universal joint, thereby allowing each jaw to articulate at said hinge.

8. A surgical instrument comprising:
   an introducer member carrying one element of a ball and socket joint at a distal end thereof;
   a first jaw having a proximal portion and a distal working end, said first jaw being rotatable at the distal end of said introducer member, said proximal portion having a first face with a first cam surface disposed therein;
   a second jaw having a proximal portion and a distal working end, said second jaw being rotatable at the distal end of said introducer member, and said proximal portion of said second jaw having a second face with a second cam surface disposed therein and the proximal portions of said first and second jaws each being connected to the other element of the ball and socket joint; and
   a cam engaging said first and second cam surfaces, wherein axial movement of said cam causes bearing contact on both said first and second cam surfaces starting at a first point and moving to a second point spaced apart from said first point to rotate said first and second jaws, said distal working ends of said first and second jaws thereby moving toward or apart from one another.

9. The device of claim 8, wherein said first and second cam surfaces have portions extending in arcs having similar radii.

10. A surgical instrument for engaging tissue, comprising:
    an elongate member defining a longitudinal axis;
    two opposing jaw structures both being movable between an open and a closed position, each said jaw structure having an opposing working face adapted for engaging tissue,
    a universal pivotal coupling connecting each of said jaw structures to an end of said elongate member, wherein said jaw structures each conjointly pivot relative to said longitudinal axis at least when in said closed position, wherein said universal pivotal coupling is a ball and socket joint; and
    a jaw structure self-aligning mechanism in said ball and socket joint.

11. The instrument of claim 10, further comprising a jaw actuating mechanism operatively connected to each of said two opposing jaw structures and to said elongate member, thereby moving said jaw structures between said open and closed positions.

12. The instrument of claim 10, further comprising a jaw locking mechanism operatively connected to said jaw structures.

13. The instrument of claim 10, further comprising a jaw actuating structure including:
    a cam surface disposed on each of said two jaw structures; and
    a cam engaging said cam surfaces, thereby rotating said two opposing jaw structures by movement of said cam.

14. A surgical instrument for engaging tissue, comprising:
    an elongated member defining a longitudinal axis;
    two opposing jaw structures both being movable between an open and a closed position, each said jaw structure having an opposing working face adapted for engaging tissue, and
    a universal pivotal coupling connecting each of said jaw structures to an end of said elongate member, wherein said jaw structures each conjointly pivot relative to said longitudinal axis at least when in said closed position;
    each said jaw structure including a hinge located intermediate a distal end of said jaw structure and said universal pivotal coupling.

15. A surgical instrument comprising:
    a handle;
    an elongate introducer member defining a first axis and having proximal and distal ends, a proximal end of said introducer member extending from said handle;
    a universal joint at said distal end of said introducer member;
    two opposing jaws each depending from said universal joint, said jaws defining a second axis and being movable between a closed position wherein said jaws converge toward said second axis and an open position wherein said jaws separate away from said second axis, whereby said universal joint allows said second axis to move relative to said first axis between parallel and non-parallel relationships in response to forces on said introducer member and said jaws;
    a jaw-actuating structure operatively connected to said jaws for causing said jaws to move between the open and closed positions with said jaws and said introducer member in a parallel or a non-parallel relationship; and
    a locking mechanism operatively connected to said jaws for releasably locking said universal point in any angular position relative to said introducer member.

16. The instrument of claim 15, wherein said universal joint further allows said second axis defined by said jaws to turn relative to said first axis with said second axis being in a parallel or non-parallel position relative to said first axis.

17. The instrument of claim 15, wherein said universal joint comprises a ball and socket joint.

18. The instrument of claim 15, wherein said universal joint comprises a flexible joint made at least partly of a resilient material.

19. The instrument of claim 15, wherein said universal joint includes a cooperating ball element and a socket element.

20. The instrument of claim 19, wherein said locking mechanism comprises means for reducing an internal dimension of said socket element to frictionally engage said ball element.

21. A surgical instrument for engaging tissue, comprising:
    a handle;
    an elongate introducer member defining a first axis and having proximal and distal ends, a proximal end of said introducer member extending from said handle;
    opposing first and second jaws, said first jaw having a first proximal jaw arm and a first distal working end, said first working end pivotably connected to said first jaw arm, said second jaw having a second proximal jaw arm and a second distal working end, said second working end pivotably connected to said second jaw arm, said first and second jaw arms pivotably connected to said distal end of said introducer member; and
    a jaw-actuating structure operatively connecting said handle and said jaws, moving said jaws between a closed position wherein said working ends converge and an open position wherein said working ends separate, and whereby said first and second working ends when engaging tissue apply pressure on the tissue over a length of said working end, thereby engaging the tissue without damage.

22. The instrument of claim 21 wherein the pivotable connection between each said jaw arm and its respective working end is a unitary resilient hinge.

23. A surgical instrument for engaging tissue, comprising:
    an elongate introducer member defining a longitudinal first axis;

two opposing jaws each coupled to a distal end of said introducer member, each said jaw having a working face adapted to engage tissue, said jaws each being moveable between a closed position wherein said working faces converge toward a second axis defined by said two jaws and an open position wherein said working faces separate away from said second axis;

a jaw actuating structure operatively connected to said jaws, thereby causing said working faces to move between the open and closed positions; and an articulating structure connecting said introducer member to said jaws, thereby allowing said jaws to articulate together relative to said first axis, wherein said articulating structure comprises a universal joint including a helically wound spring.

24. A surgical instrument for engaging tissue, comprising:

an elongate introducer member defining a longitudinal first axis;

two opposing jaws each coupled to a distal end of said introducer member, each said jaw having a working face adapted to engage tissue, said jaws each being moveable between a closed position wherein said working faces converge toward a second axis defined by said two jaws and an open position wherein said working faces separate away from said second axis;

a jaw actuating structure operatively connected to said jaws, thereby causing said working faces to move between the open and closed positions;

an articulating structure connecting said introducer member to said jaws, thereby allowing said jaws to articulate together relative to said first axis; and a jaw self-aligning mechanism operatively connected to said jaws structures, thereby releasably maintaining said jaws in substantial alignment with said first axis when said jaws are moved toward the closed position from the open position;

wherein said articulating structure comprises a ball and socket joint and said self-aligning mechanism comprises a plurality of spring elements incorporated into proximal portions of said jaws that releasably engage an edge portion of said socket.

25. A surgical instrument for engaging tissue, comprising:

an elongate introducer member defining a longitudinal first axis;

two opposing jaws each coupled to a distal end of said introducer member, each said jaw having a working face adapted to engage tissue, said jaws each being moveable between a closed position wherein said working faces converge toward a second axis defined by said two jaws and an open position wherein said working faces separate away from said second axis;

a jaw actuating structure operatively connected to said jaws, thereby causing said working faces to move between the open and closed positions;

an articulating structure connecting said introducer member to said jaws, thereby allowing said jaws to articulate together relative to said first axis;

wherein said articulating structure comprises a universal-type joint; and a reciprocating sleeve slidably mounted around said introducer member, wherein a slidable disposition of said reciprocating sleeve over said universal-type joint locks said universal-type joint.

26. A surgical instrument for engaging tissue, comprising:

an elongate introducer member defining a longitudinal first axis;

two opposing jaws each coupled to a distal end of said introducer member, each said jaw having a working face adapted to engage tissue, said jaws each being moveable between a closed position wherein said working faces converge toward a second axis defined by said two jaws and an open position wherein said working faces separate away from said second axis;

a jaw actuating structure operatively connected to said jaws, thereby causing said working faces to move between the open and closed positions; and an articulating structure connecting said introducer member to said jaws, thereby allowing said jaws to articulate together relative to said first axis;

each said jaw further including a hinge located intermediate its distal end and said articulating structure, thereby allowing each said jaw to further articulate at said hinge.

27. A surgical instrument for engaging tissue, comprising:

an elongate member defining a longitudinal axis;

two opposing jaw structures both being movable between an open and a closed position, each said jaw structure having an opposing working face; and a pivotal coupling connecting each of said jaw structures to an end of said elongate member, wherein said jaw structures each conjointly pivot relative to said longitudinal axis at least when in said closed position;

each said jaw including a hinge located intermediate a distal end of said jaw and said pivotal coupling.

\* \* \* \* \*